(12) United States Patent
Thakur et al.

(10) Patent No.: US 10,485,978 B2
(45) Date of Patent: *Nov. 26, 2019

(54) PACING SITE AND CONFIGURATION OPTIMIZATION USING A COMBINATION OF ELECTRICAL AND MECHANICAL INFORMATION

(71) Applicant: Cardiac Pacemakers, Inc., St. Paul, MN (US)

(72) Inventors: Pramodsingh Hirasingh Thakur, Woodbury, MN (US); Yinghong Yu, Shoreview, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/921,949

(22) Filed: Mar. 15, 2018

(65) Prior Publication Data

US 2018/0200521 A1 Jul. 19, 2018

Related U.S. Application Data

(63) Continuation of application No. 15/598,594, filed on May 18, 2017, now Pat. No. 9,950,177, which is a
(Continued)

(51) Int. Cl.
*A61N 1/368* (2006.01)
*A61N 1/365* (2006.01)
(Continued)

(52) U.S. Cl.
CPC ....... *A61N 1/3686* (2013.01); *A61N 1/36578* (2013.01); *A61N 1/36585* (2013.01);
(Continued)

(58) Field of Classification Search
CPC .............. A61N 1/3686; A61N 1/36578; A61N 1/35686; A61N 1/3702; A61N 1/371
See application file for complete search history.

(56) References Cited

U.S. PATENT DOCUMENTS 8,617,082 B2 * 12/2013 Zhang .................. A61B 5/0006
600/528
9,272,148 B2 * 3/2016 Ghosh ................ A61N 1/36585
(Continued)

OTHER PUBLICATIONS

"U.S. Appl. No. 14/812,372, Corrected Notice of Allowance dated Apr. 7, 2017", 2 pgs.
(Continued)

*Primary Examiner* — Paula J Stice
(74) *Attorney, Agent, or Firm* — Schwegman Lundberg & Woessner, P.A.

(57) ABSTRACT

An apparatus comprises a cardiac signal sensing circuit configured to sense a plurality of intrinsic cardiac signals using a plurality of cardiac pacing sites, a heart sound sensing circuit, a stimulus circuit configured to provide an electrical cardiac pacing stimulus to the plurality of pacing sites, and a control circuit electrically coupled to the cardiac signal sensing circuit and the stimulus circuit. The control circuit includes a pacing site locating circuit configured to generate an indication of a preferred pacing site as one of a) a subset of the respective cardiac pacing sites selected using the intrinsic ventricular activation time interval value, from which subset the preferred pacing site is selected using the heart sound characteristic value; or b) a subset of the respective cardiac pacing sites selected using the heart sound characteristic value, from which subset the preferred pacing site is selected using the ventricular activation time interval value.

20 Claims, 4 Drawing Sheets

Related U.S. Application Data continuation of application No. 14/812,372, filed on Jul. 29, 2015, now Pat. No. 9,707,401.

(60) Provisional application No. 62/030,939, filed on Jul. 30, 2014.

(51) Int. Cl.
  *A61N 1/37* (2006.01)
  *A61B 7/04* (2006.01)

(52) U.S. Cl.
  CPC .................. *A61B 7/04* (2013.01); *A61N 1/371* (2013.01); *A61N 1/3702* (2013.01)

(56) References Cited

U.S. PATENT DOCUMENTS

| | | | |
|---|---|---|---|
| 9,707,401 | B2 | 7/2017 | Thakur et al. |
| 2004/0064162 | A1 | 4/2004 | Manrodt et al. |
| 2006/0293714 | A1 | 12/2006 | Salo et al. |
| 2009/0210024 | A1 | 8/2009 | Brooke |
| 2012/0136406 | A1 | 5/2012 | Min |
| 2012/0203295 | A1 | 8/2012 | Maskara et al. |
| 2012/0303078 | A1 | 11/2012 | Li et al. |
| 2016/0030747 | A1 | 2/2016 | Thakur et al. |
| 2017/0252565 | A1 | 9/2017 | Thakur et al. |

OTHER PUBLICATIONS

"U.S. Appl. No. 14/812,372, Non Final Office Action dated Nov. 25, 2016", 12 pgs.

"U.S. Appl. No. 14/812,372, Notice of Allowance dated Mar. 16, 2017", 8 pgs.

"U.S. Appl. No. 14/812,372, Response filed Jan. 10, 2017 to Non Final Office Action dated Nov. 25, 2016", 12 pgs.

"U.S. Appl. No. 14/812,372, Response filed Jun. 16, 2016 to Restriction Requirement dated Apr. 26, 2016", 9 pgs.

"U.S. Appl. No. 14/812,372, Response filed Sep. 7, 2016 to Restriction Requirement dated Jul. 11, 2016", 8 pgs.

"U.S. Appl. No. 14/812,372, Restriction Requirement dated Apr. 26, 2016", 9 pgs.

"U.S. Appl. No. 14/812,372, Restriction Requirement dated Jul. 11, 2016", 6 pgs.

"U.S. Appl. No. 15/598,594, Final Office Action dated Oct. 6, 2017", 6 pgs.

"U.S. Appl. No. 15/598,594, Non Final Office Action dated Jun. 27, 2017", 11 pgs.

"U.S. Appl. No. 15/598,594, Notice of Allowance dated Dec. 13, 2017", 7 pgs.

"U.S. Appl. No. 15/598,594, Response filed Sep. 5, 2017 to Non Final Office Action dated Jun. 27, 2017", 14 pgs.

"U.S. Appl. No. 15/598,594, Response filed Nov. 22, 2017 to Final Offie Action dated Nov. 22, 2017", 8 pgs.

\* cited by examiner

PACING SITE AND CONFIGURATION OPTIMIZATION USING A COMBINATION OF ELECTRICAL AND MECHANICAL INFORMATION

CLAIM OF PRIORITY

This application is a continuation of U.S. application Ser. No. 15/598,594, filed May 18, 2017, which is a continuation of U.S. application Ser. No. 14/812,372, filed Jul. 29, 2015, now issued as U.S. Pat. No. 9,707,401, which claims the benefit of priority under 35 U.S.C. § 119(e) of U.S. Provisional Patent Application Ser. No. 62/030,939, filed on Jul. 30, 2014, each of which is herein incorporated by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Medical devices also include wearable medical devices such as wearable cardioverter defibrillators (WCDs). WCDs are monitors that include surface electrodes. The surface electrodes are arranged to provide one or both of monitoring surface electrocardiograms (ECGs) and delivering cardioverter and defibrillator shock therapy.

Some medical devices include one or more sensors to monitor different physiologic aspects of the patient. For example, the devices may derive measurements associated with a cardiac depolarization of the patient. Such monitoring devices can be implantable or wearable and the measurements can provide useful information concerning the cardiac health of the patient.

By monitoring cardiac signals indicative of expansions or contractions, IMDs can detect abnormally slow heart rate, or bradycardia. In response to an abnormally slow heart rate some CFM devices deliver electrical pacing stimulation energy to induce cardiac depolarization and contraction. The pacing stimulation energy is delivered to provide a depolarization rate that improves hemodynamic function of the patient. Delivery of pacing therapy should be optimized to ensure therapy delivery and yet avoid unnecessary stress on the heart and unnecessary reduction of battery life. Optimal selection of the site for delivery of the pacing therapy can be part of pacing therapy optimization. Optimal site selection can lead to optimized use of pacing energy and to improved hemodynamic function of the patient or subject.

OVERVIEW

This document relates generally to systems, devices, and methods that provide electrical pacing therapy to the heart of a patient or subject. In particular it relates to, systems, devices, and methods that determine a preferred site of the heart to provide pacing therapy.

An apparatus example includes a cardiac signal sensing circuit that senses a plurality of intrinsic cardiac signals using a plurality of cardiac pacing sites, a stimulus circuit that provides an electrical cardiac pacing stimulus to the plurality of pacing sites, a heart sound sensing circuit that produces a paced heart sound signal representative of mechanical cardiac activity resulting from an electrical stimulus delivered at the corresponding cardiac pacing site, and a control circuit electrically coupled to the cardiac signal sensing circuit, the heart sound sensing circuit, and the stimulus circuit. The control circuit includes a signal processing circuit that determines intrinsic ventricular activation time interval values for the sensed cardiac signals; and determines values of a heart sound characteristic for the sensed heart sound signals. The control circuit also includes a pacing site locating circuit that generates an indication of a preferred pacing site as one of a) a subset of the respective cardiac pacing sites selected using the intrinsic ventricular activation time interval value, from which subset the preferred pacing site is selected using the heart sound characteristic value, or b) a subset of the respective cardiac pacing sites selected using the heart sound characteristic value, from which subset the preferred pacing site is selected using the ventricular activation time interval value.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

As explained previously, pacing therapy should be optimized for a patient. This can include optimizing one or both of the pacing site and the pacing energy used to deliver the therapy. The pacing site selected to deliver the pacing stimulus can have a significant impact on the therapy. Often a tissue site having the longest electrical activation delay is desired as a pacing site in order to reduce the activation delay. However, the pacing site with the longest activation delay may be within a region of partly ischemic tissue. Pacing at a partly ischemic tissue site is often ineffective. Confirming tissue viability at a desired pacing site can be part of optimizing pacing therapy for the patient.

Figure 1:
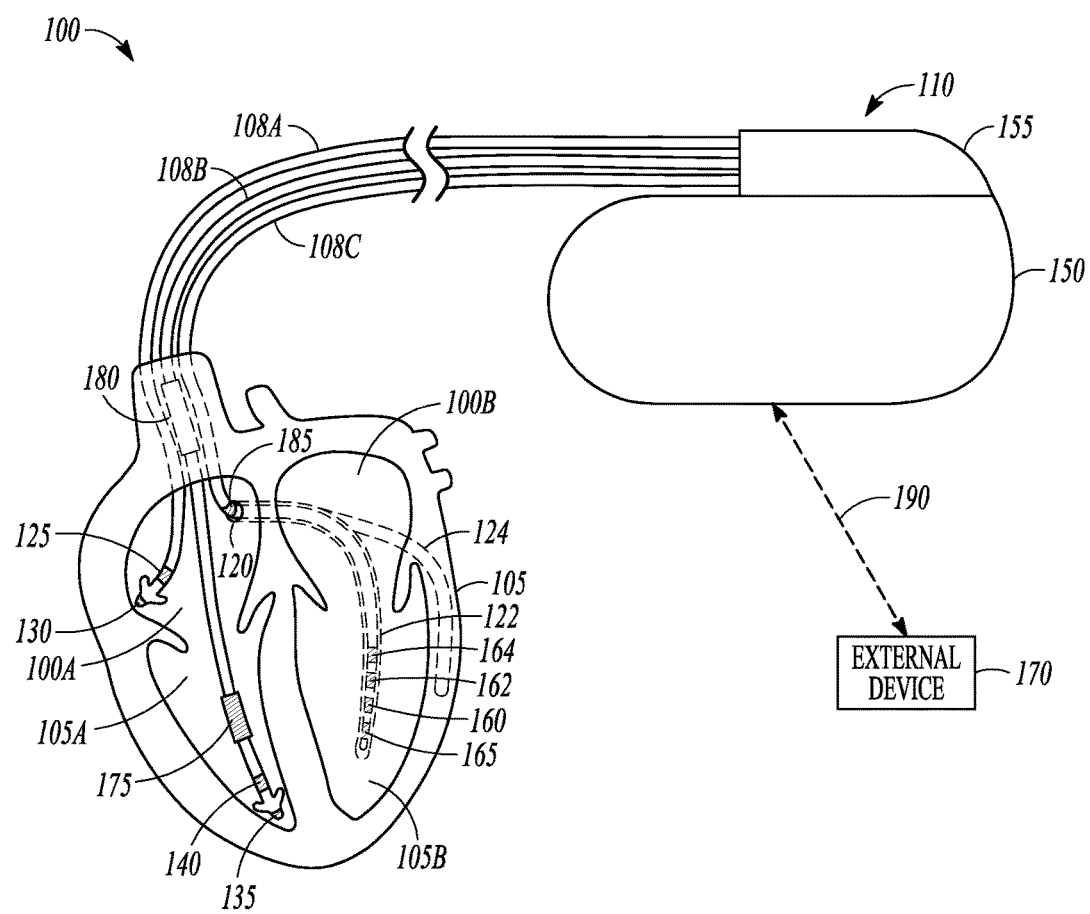
FIG. 1 is an illustration of an example of portions of a system that includes an IMD.

FIG. 1 is an illustration of portions of a system that uses an IMD 110. Examples of IMD 110 include, without limitation, a pacemaker, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMB 110 can include a third cardiac lead 108C attached to the IMB 110 through the header 155. The third cardiac lead 108C includes electrodes 160, 162, 164, and 165 placed in a coronary vein lying epicardially on the left ventricle (LV) 105B via the coronary vein. The third cardiac lead 108C may include anywhere from two to eight electrodes, and may include a ring electrode 185 positioned near the coronary sinus (CS) 120.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

Figure 2:
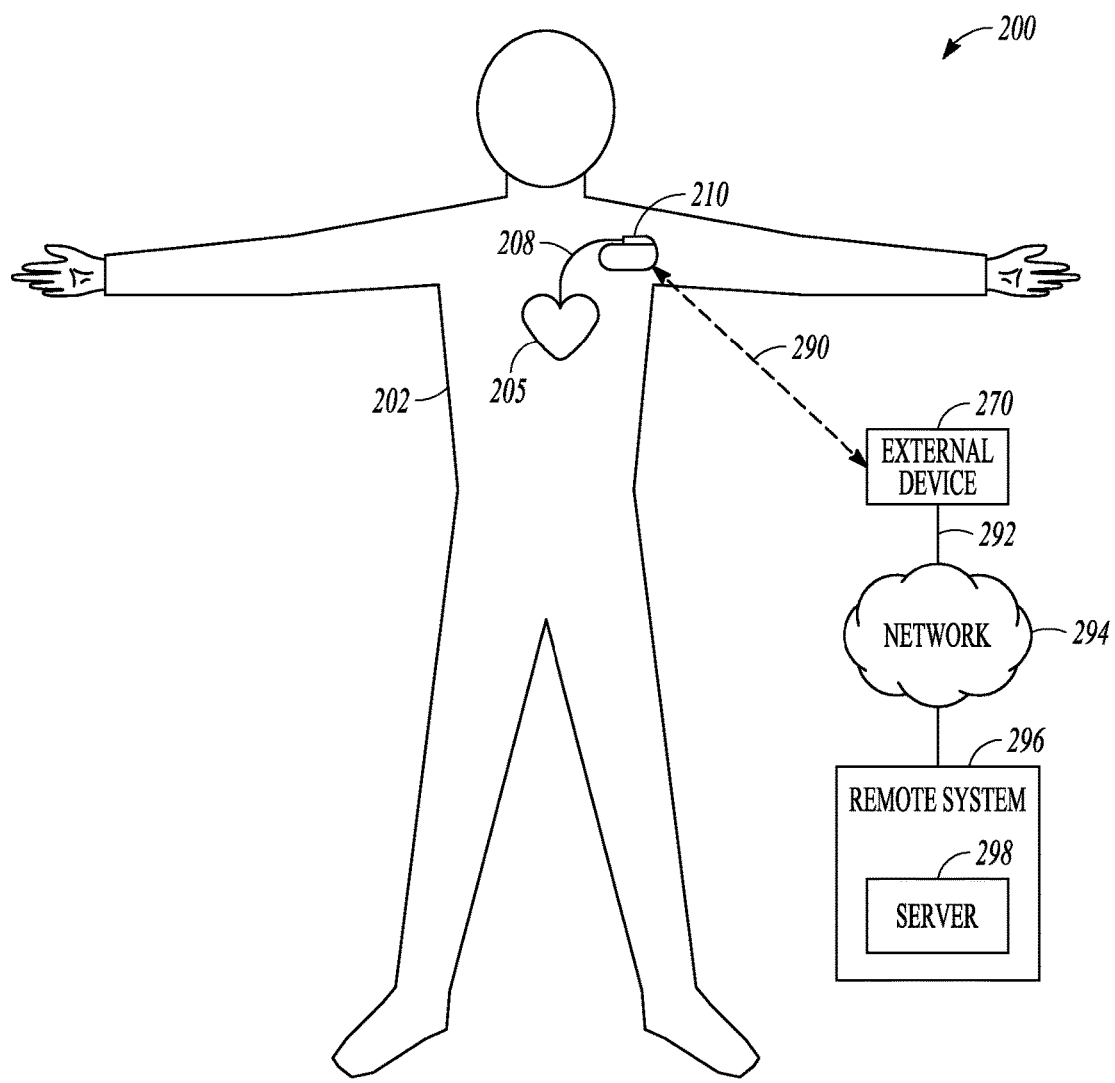
FIG. 2 is an illustration of portions of another system that uses an IMD.

FIG. 2 is an illustration of portions of another system 200 that uses an IMD 210 to provide a therapy to a patient 202. The system 200 typically includes an external device 270 that communicates with a remote system 296 via a network 294.

The network 294 can be a communication network such as a phone network or a computer network (e.g., the internet). In some examples, the external device includes a repeater and communicated via the network using a link 292 that may be wired or wireless. In some examples, the remote system 296 provides patient management functions and may include one or more servers 298 to perform the functions.

Providing pacing energy at an improper pacing site or location can lead to ineffective activation of myocardial tissue. It may be desirable to have an IMD or other medical device automatically run tests to determine the best pacing site or sites, and either propose to the caregiver that these sites be used to provide the pacing therapy or automatically initiate delivery of pacing therapy to a determined optimal pacing site.

Figure 3:
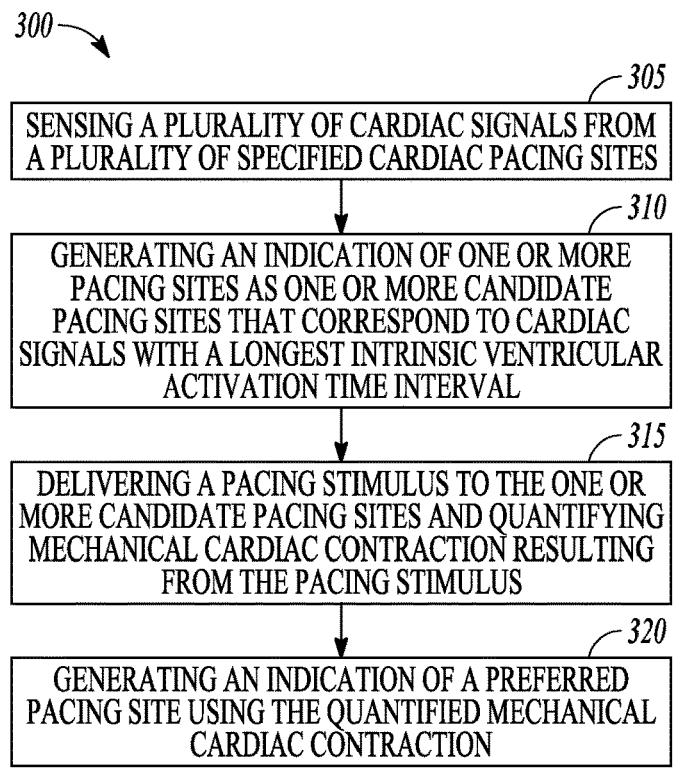
FIG. 3 is a flow diagram of an example of a method of operating a medical device system.

FIG. 3 is a flow diagram of an example of a method 300 of operating a medical device. At 305, multiple cardiac signals are sensed. A cardiac signal is an electrical signal representative of electrical cardiac activity. The cardiac signals are sensed using a plurality of specified cardiac pacing sites.

A specific pacing site can refer to a specific combination of electrodes. In some examples, the electrodes are implantable and are electrically connectable to an IMD. In certain examples, the pacing site includes an electrode pair. The first electrode of the pacing site is common when sensing the cardiac signals and the second electrode is selectable. For instance, in the example of FIG. 1, electrode 165 may be the first electrode, and three cardiac signals are sensed using one of ring electrodes 160, 162 or 164 as the second electrode of a bipolar electrode pair. The implantable device may be configured (e.g., by programming) to advance through specified pacing sites to sense a cardiac signal and perform one or more measurements.

A specific pacing site can refer to a lead that includes at least one electrode. The lead can be electrically connectable to a pacing system analyzer (PSA). A user (e.g., a physician) can position the lead at pacing sites of interest and trigger the medical device to sense a cardiac signal to perform one or more measurements.

Using a cardiac signal sensed at a pacing site, the medical device determines the time interval or time duration of an intrinsic ventricular activation. As an example not intended to be limiting, the medical device may measure an interval between a sensed Q-wave and a sensed depolarization of the left ventricle (LV) and the intrinsic ventricular activation time interval is a Q-LV time interval. Other examples of an intrinsic ventricular activation interval are provided elsewhere herein.

At 310, an indication is generated by the medical device of one or more pacing sites as candidate pacing sites. A candidate pacing site is a pacing site that corresponds to cardiac signals with a long intrinsic ventricular activation time interval. In certain variations, the medical device identifies a candidate pacing site when its corresponding intrinsic ventricular activation interval is longer than a specified threshold value. In certain variations, the medical device identifies candidate pacing sites as the pacing sites having the N longest intrinsic ventricular activation intervals, where N is a positive integer.

It is sometimes desired to select the site corresponding to the longest ventricular activation interval as the pacing site. By implication, the site corresponding to the longest interval is the latest activation site, and pacing at such a site may reduce the time for ventricular activation. However, the site corresponding to the longest intrinsic ventricular activation interval may correspond to a site of ischemic tissue, and providing pacing therapy at such an ischemic site is likely to be ineffective. A better approach is to determine the tissue viability of a candidate site before that site is selected as the preferred pacing site for the subject.

At 315, a pacing stimulus is delivered to the identified candidate pacing sites by the medical device. The medical device quantifies the mechanical cardiac contraction resulting from the pacing stimulus. The mechanical cardiac contraction refers to the actual physical contraction of the heart. This is different from an electrical depolarization signal. The mechanical activation may be useful to determine tissue viability for pacing therapy.

As an example, the medical device may quantify the mechanical cardiac contraction using, among other things, a sensed heart sound signal. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. A heart sound signal can be an electrical signal representative of one or more heart sounds produced by a heart sound sensor circuit (e.g., an accelerometer). The medical device may use a parameter measured using the heart sound signal (e.g., heart sound signal amplitude) to quantify the mechanical cardiac contraction.

At 320, the medical device generates an indication of a preferred pacing site using the quantified mechanical cardiac contraction and provides the indication to at least one of a user or process. The medical device may use the indication to display preferred pacing sites to the user, or the medical device may communicate the indication to a process (e.g., executing on a separate device), and that process may store or display identified preferred pacing sites.

Figure 4:
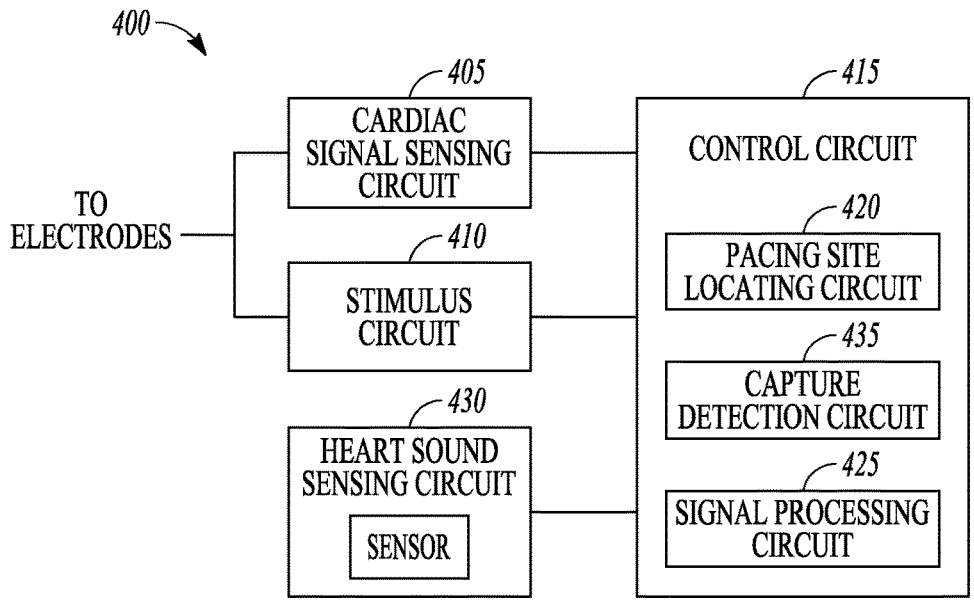
FIG. 4 is a block diagram of portions of an example of a medical device system that can determine a preferred site to deliver pacing therapy.

FIG. 4 is a block diagram of portions of an example of a medical device 400 operable to automatically determine preferred sites to deliver pacing therapy. The device 400 includes a cardiac signal sensing circuit 405 that senses a plurality of intrinsic cardiac signals using a plurality of cardiac pacing sites. A cardiac signal is an electrical signal representative of electrical cardiac activity (e.g., a signal representative of electrical action potential of cardiac tissue).

As explained previously, a cardiac pacing site can refer to a specific combination of cardiac electrodes. For instance, in the IMD example of FIG. 1 a pacing site can include any combination of two of LV electrodes 160, 162, 164 and 165 as a bipolar electrode pair. In other examples, a pacing site may include any of LV electrodes 160, 162, 164 and 165 as a pacing cathode and an electrode formed in IMB housing 150 or header 155 as the pacing anode. Other pacing sites can include combinations of RV and LV electrodes. In some variations, the pacing sites include more than two electrodes. For instance, two electrodes may be electrically connected together for as a combined electrode. The medical device 400 may include a switch matrix circuit (not shown) to selectively connect electrode combinations to the cardiac signal sensing circuit 405. In some examples, the device is PSA that is electrically connectable to one or more cardiac pacing leads that include one or more electrodes that can be positioned at pacing sites for testing.

The device 400 also includes a stimulus circuit 410 that provides an electrical cardiac pacing stimulus to the plurality of pacing sites, and a control circuit 415 electrically coupled to the cardiac signal sensing circuit 405 and the stimulus circuit 410. The control circuit 415 can include a processor such as a microprocessor, a digital signal processor, application specific integrated circuit (ASIC), or other type of processor, interpreting or executing instructions in software modules or firmware modules. In some examples, the control circuit 415 includes a sequencer. A sequencer refers to a state machine or other circuit that sequentially steps through a fixed series of steps to perform one or more functions. The steps are typically implemented in hardware or firmware. The control circuit 415 includes other circuits or sub-circuits to perform the functions described. These circuits may include software, hardware, firmware or any combination thereof. Multiple functions can be performed in one or more of the circuits or sub-circuits as desired.

The control circuit 415 includes a pacing site locating circuit 420 to perform a test to determine one or more preferred pacing sites for the subject. The pacing site locating circuit 420 generates an indication of one or more pacing sites corresponding to cardiac signals with a longest intrinsic ventricular activation time interval as one or more candidate pacing sites. In certain variations, the indication may be an electrical signal communicated to a process, or an identifier of a pacing site stored in memory integral to, or electrically coupled to, the control circuit 415.

As explained above, in some examples the intrinsic ventricular activation interval can be the Q-LV time interval. The device 400 can include a signal processing circuit 425 that detects a first fiducial in a sensed cardiac signal indicative of a Q-wave and a second cardiac signal fiducial indicative of LV depolarization. The signal processing circuit 425 determines the Q-LV time interval between the first cardiac signal fiducial and the second cardiac signal fiducial. The pacing site locating circuit 420 indicates an electrode site as a candidate pacing site when a corresponding Q-LV time interval is longer than a specified threshold interval value.

In some examples, the intrinsic ventricular activation interval is a time interval between intrinsic RV depolarization and intrinsic LV depolarization. The signal processing circuit 425 detects a first cardiac signal fiducial indicative of a RV depolarization and a second cardiac signal fiducial indicative of LV depolarization and determines a RV-LV time interval between the first cardiac signal fiducial and the second cardiac signal fiducial. The pacing site locating circuit 420 indicates an electrode site as a candidate pacing site when a corresponding RV-LV time interval is longer than a specified threshold interval value.

In some examples, the intrinsic ventricular activation interval is an intrinsic atrial-ventricular (A-V) delay interval. The signal processing circuit 425 detects a first cardiac signal fiducial indicative of atrial depolarization (e.g., right atrial depolarization) and a second cardiac signal fiducial indicative of LV depolarization and determines an A-V delay between the first cardiac signal fiducial and the second cardiac signal fiducial. The pacing site locating circuit 420 indicates an electrode site as a candidate pacing site when a corresponding A-V delay is longer than a specified threshold interval value.

Identifying the sites with the longest intrinsic ventricular activation time interval can be the primary method of identifying candidate pacing sites. The candidate sites can be further evaluated by the pacing site locating circuit 420 according to their tissue viability. The pacing site locating circuit 420 initiates delivery of a pacing stimulus to the one or more candidate pacing sites by the stimulus circuit 410 and quantifies the mechanical cardiac contraction resulting from the pacing stimulus. The pacing site locating circuit 420 generates an indication of a preferred pacing site using the quantified mechanical cardiac contraction.

In some examples, heart sounds are used to quantify the mechanical cardiac contraction. The device 400 may include a heart sound sensing circuit 430 that produces a sensed heart sound signal. Some examples of a heart sound sensing circuit include an accelerometer and a microphone. The heart sound sensing circuit 430 may produce an electrical signal representative of the S1 heart sound. In certain examples, the pacing site locating circuit 420 determines S1 heart sound amplitude resulting from the pacing stimulus and generates an indication of the preferred pacing site as the pacing site corresponding to the largest S1 heart sound amplitude. In certain examples, the pacing site locating circuit 420 determines S1 heart sound amplitude for an intrinsic depolarization and S1 heart sound amplitude for a paced depolarization. The pacing site locating circuit 420 generates an indication of the preferred pacing site as the pacing site corresponding to the largest amplitude difference between the intrinsic S1 heart sound and the paced S1 heart sound.

In some examples, a systolic time interval is used to quantify the mechanical cardiac contraction. An example of a systolic time interval useful to quantify a mechanical cardiac contraction is a heart sound pre-ejection period or HSPEP. To measure HSPEP, the signal processing circuit 425 may detect a cardiac signal fiducial indicative of an R-wave and a heart sound signal fiducial indicative of an S1 heart sound. The signal processing circuit 425 determines an intrinsic R-S1 time interval and a paced R-S1 time interval. The pacing site locating circuit 420 indicates a candidate pacing site as the preferred pacing site when the candidate pacing site corresponds to the pacing site having the largest difference between the paced R-S1 time interval and the intrinsic R-S1 time interval. This largest difference corresponds to the pacing site where HSPEP can be most improved through pacing therapy.

In some examples, detection of cardiac capture is used to quantify the mechanical cardiac contraction. Cardiac capture refers to when delivery of electrical pacing stimulation energy induces cardiac depolarization and cardiac contraction. The control circuit 415 can include a capture detection circuit 435 that detects cardiac capture in response to the pacing stimulus. The pacing site locating circuit 420 indicates a candidate pacing site as the preferred pacing site when delivery of the pacing stimulus at the candidate pacing site resulted in cardiac capture.

In some variations, the capture detection circuit 435 delivers series of pacing stimuli to a candidate pacing site. The series may include a successive reduction of the energy of the pacing pulses. A first pacing pulse that will likely induce capture is delivered. The energy of subsequent pacing pulses is reduced in steps until the device verifies that failure to induce capture has occurred. Alternatively, the sequence may include increasing the energy of the pacing pulses. A first pacing pulse that is below a threshold likely to induce capture is delivered. The energy of subsequent pacing pulses is increased in steps until the device verifies that capture was induced. The device uses information obtained from the threshold test to recommend a pacing output setting, to automatically adjust a pacing output setting, or to identify preferred pacing sites.

The indication of one or more preferred pacing sites can be provided to a user or process. In some examples, the cardiac signal sensing circuit 405, the stimulus circuit 410 and the control circuit 415 are included in a PSA. The PSA is connectable to one or more leads including at least one electrode configured for positioning at the pacing sites. The preferred pacing site may be presented to a user on a display of the device. A clinician may then arrange cardiac leads for pacing at the indicated preferred pacing site using information of the preferred pacing site.

In some examples, the cardiac signal sensing circuit 405 and the stimulus circuit 410 are included in an IMD that is connectable to a plurality of electrodes and combinations of the plurality of electrodes correspond to the plurality of pacing sites. The control circuit 415 and the pacing site locating circuit 420 can be included in an external device used to program the IMD. The preferred pacing site may be presented to a user on a display of the device. The user of the external device may then configure the IMD for pacing using information of the preferred pacing site.

In some examples, the cardiac signal sensing circuit 405, the stimulus circuit 410 and the control circuit 415 are included in an IMD connectable to a plurality of electrodes, and combinations of the plurality of electrodes correspond to the plurality of pacing sites. The indication of the preferred pacing site may be communicated (e.g., via wireless telemetry) to a second device where the indication can be displayed. The IMD can then be configured for pacing (e.g., by programming) using information of the preferred pacing site.

In some examples, the control circuit 415 is configured to recurrently initiate a pacing site locating procedure. The procedure can be initiated while the patient is ambulatory and the patient does not need to be at a clinic for the procedure to be performed. The test may be initiated by an IMD or by an external device that communicates with the IMD. When initiated by the control circuit 415, the pacing site locating circuit senses a plurality of ventricular activation time intervals using a plurality of combinations of electrodes to identify cone or more candidate pacing sites and delivers a pacing stimulus to the one or more candidate pacing sites and quantify a mechanical cardiac contraction resulting from the pacing stimulus, and changes the pacing site according to the quantified mechanical cardiac contraction. In certain examples, the IMD communicates information associated with the procedure to an external device which may change the pacing site accordingly.

The examples described previously refer to using intrinsic ventricular activation information as a method of identifying candidate pacing sites or a subset of pacing sites from which one or more preferred pacing sites are identified. Mechanical activation is then used to assess tissue viability of candidate sites to determine preferred pacing sites. Another approach is to use mechanical activation information to first identify a subset of the respective pacing sites as candidate pacing sites.

Figure 5:
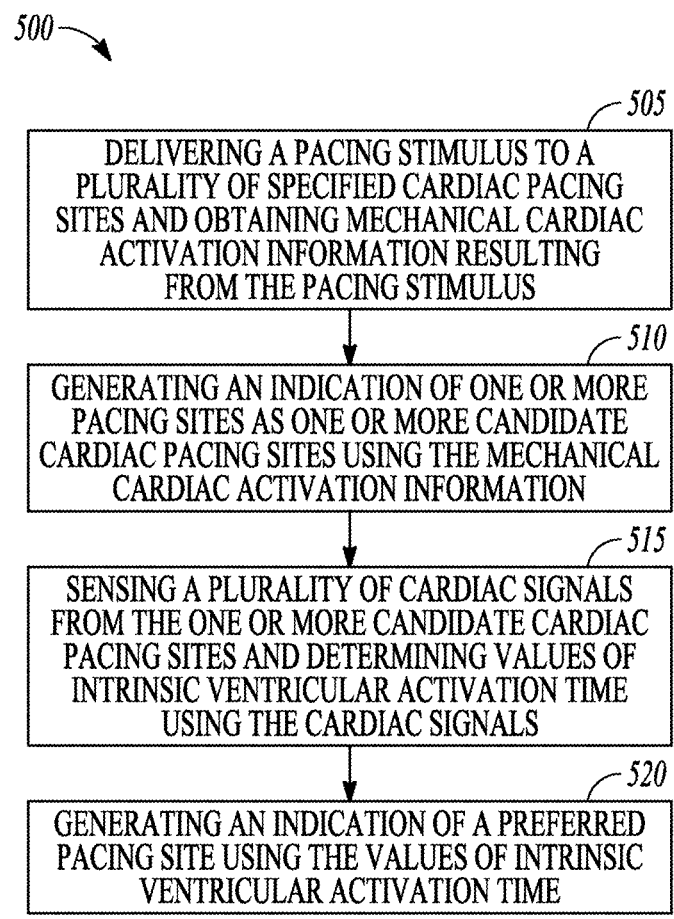
FIG. 5 is a flow diagram of another example of a method of operating a medical device system.

FIG. 5 is a flow diagram of an example of a method 300 of operating a medical device. At 505, a pacing stimulus is delivered to a plurality of specified cardiac pacing sites. Mechanical cardiac activation information resulting from the pacing stimulus is then obtained. Examples of mechanical cardiac activation information include heart sound information and cardiac capture information. The mechanical activation information can be used as a primary tissue viability screen. At 510, an indication of one or more pacing sites as one or more candidate pacing sites is generated using the mechanical activation information.

Device-based measurements of mechanical activation can be noisy. If the mechanical activation information includes differences between an intrinsic heart sound characteristic and a paced heart sound characteristic, some of the pacing sites may only show an incremental benefit from one to another, which can make the selection between pacing sites difficult. Intrinsic ventricular activation information may be useful to further screen the subset of candidate pacing sites to determine one or more preferred pacing sites.

At 515, a plurality of cardiac signals are sensed from the one or more candidate pacing sites and values of intrinsic ventricular activation time are determined using the sensed cardiac signals. At 520, an indication of a preferred pacing site is generated using the values of intrinsic ventricular activation time, such as a pacing site having the greatest value of ventricular activation time for example.

Returning to FIG. 4, according to some examples the device 400 includes the heart sound sensing circuit 430, the stimulus circuit 410, the cardiac signal sensing circuit 405, and the control circuit 415. The pacing site locating circuit 420 measures the amplitude of an intrinsic S1 heart sound using the heart sound signal produced by the heart sound sensing circuit 430. The pacing site locating circuit 420 also initiates delivery of an electrical cardiac pacing stimulus to the plurality of pacing sites and measures the amplitude of a paced S1 heart sound resulting from the pacing stimulus.

The pacing site locating circuit 420 generates an indication of a pacing site as a candidate pacing site when a change between the intrinsic S1 amplitude and the paced S1 amplitude is greater than a specified threshold amplitude value. The candidate pacing sites thus correspond to those sites with the most improvement between intrinsic depolarization and paced depolarization. In some examples, a maximum amplitude change is determined from the measured amplitudes and used to determine a threshold amplitude value (e.g., a threshold of 50% of the measured maximum amplitude change). The pacing sites satisfying the threshold are indicated to be candidate pacing sites.

Intrinsic cardiac signals are sensed by the cardiac signal sensing circuit 405 for the candidate pacing sites. The intrinsic cardiac signals may be sensed for each of the specified pacing site as the heart sound signals are sensed, or intrinsic signals may only be sensed for the candidate pacing sites. The pacing site locating circuit 420 measures the intrinsic ventricular activation time interval using the plurality of sensed cardiac signals. The device 400 may include the signal processing circuit 425 and the intrinsic ventricular activation time interval may include one or more of the Q-LV interval, the RV-LV interval, and the AV delay. The intervals can be determined using the methods previously described. The pacing site locating circuit 420 generates an indication of a candidate pacing site as a preferred pacing site when the candidate pacing site corresponds to a longest intrinsic ventricular activation time.

According to some examples, detection of cardiac capture is used to identify a subset of the respective pacing sites as candidate pacing sites. The device 400 includes the stimulus circuit 410, the cardiac signal sensing circuit 405, and the control circuit 415. The control circuit includes the capture detection circuit 435. Electrical stimuli are provided to the pacing sites and the pacing site locating circuit 420 generates an indication of a pacing site as a candidate pacing site when cardiac capture is detected for a pacing site. A preferred site is then chosen using sensed intrinsic cardiac signals. The pacing site locating circuit 420 generates an indication of a candidate pacing site as a preferred pacing site when the candidate pacing site corresponds to a longest intrinsic ventricular activation time.

The device-based measurements may be useful to identify weak responders to pacing therapy. A weak responder may be a subject with a small difference between an intrinsic S1 amplitude and a paced S1 amplitude at one or more pacing sites identified as having long intrinsic ventricular activation times. When this is detected, the pacing site locating circuit 420 may generate an indication of a weak responder and provide the indication to at least one of a user or process.

Finding an optimal pacing site should be part of optimizing pacing therapy. Automaticity in finding the optimal site simplifies the site selection process, which may result in more caregivers locating the optimal site for their patients. Using tissue viability information may improve the likelihood of finding the optimal pacing site.

ADDITIONAL NOTES AND EXAMPLES

Example 1 includes subject matter (such as an apparatus) comprising a cardiac signal sensing circuit configured to sense a plurality of cardiac signals, from respective cardiac pacing sites, wherein a cardiac signal is representative of electrical cardiac activity, a stimulus circuit configured to provide an electrical cardiac pacing stimulus to the plurality of pacing sites, a heart sound sensing circuit configured to produce a paced heart sound signal representative of mechanical cardiac activity resulting from an electrical stimulus delivered at the corresponding cardiac pacing site, and a control circuit electrically coupled to the cardiac signal sensing circuit, the heart sound sensing circuit, and the stimulus circuit. The control circuit includes a signal processing circuit and a pacing site location circuit. The signal processing circuit is configured to determine intrinsic ventricular activation time interval values for the sensed cardiac signals, and determine values of a heart sound characteristic for the sensed heart sound signals. The pacing site locating circuit is configured to generate an indication of a preferred pacing site as one of: a) a subset of the respective cardiac pacing sites selected using the intrinsic ventricular activation time interval value, from which subset the preferred pacing site is selected using the heart sound characteristic value; or b) a subset of the respective cardiac pacing sites selected using the heart sound characteristic value, from which subset the preferred pacing site is selected using the ventricular activation time interval value.

In Example 2, the subject matter of Example 1 optionally includes a heart sound sensing circuit configured to produce an electrical signal representative of the S1 heart sound, the signal processing circuit is configured to determine S1 heart sound amplitude resulting from the pacing stimulus, and optionally includes a pacing site locating circuit configured to generate an indication of a preferred pacing site as one of: a) a subset of the respective cardiac pacing sites selected using the intrinsic ventricular activation time interval value, from which subset the preferred pacing site is selected using the S1 heart sound amplitude; or b) a subset of the respective cardiac pacing sites selected using the S1 heart sound amplitude, from which subset the preferred pacing site is selected using the ventricular activation time interval value.

In Example 3, the subject matter of one or any combination of Examples 1 and 2 optionally includes a heart sound sensing circuit configured to produce an electrical heart sound signal representative of the S1 heart sound, a signal processing circuit configured to detect a cardiac signal fiducial indicative of an R-wave, a heart sound signal fiducial indicative of an S1 heart sound and determine an intrinsic R-S1 time interval and a paced R-S1 time interval, and optionally includes a pacing site locating circuit configured to generate an indication of a preferred pacing site as one of: a) a subset of the respective cardiac pacing sites selected using the intrinsic ventricular activation time interval value, from which subset the preferred pacing site is selected using a difference between the paced R-S1 time interval and the intrinsic R-S1 time interval; or b) a subset of the respective cardiac pacing sites selected using the difference between the paced R-S1 time interval and the intrinsic R-S1 time interval, from which subset the preferred pacing site is selected using the ventricular activation time interval value.

In Example 4, the subject matter of one or any combination of Examples 1-3 optionally includes a signal processing circuit configured to detect a first cardiac signal fiducial indicative of a Q-wave, a second cardiac signal fiducial indicative of left ventricular (LV) depolarization and determine a Q-LV time interval between the first cardiac signal fiducial and the second cardiac signal fiducial, and optionally includes a pacing site locating circuit configured to generate an indication of a preferred pacing site as one of: a) a subset of the respective cardiac pacing sites selected using the Q-LV time interval, from which subset the preferred pacing site is selected using the heart sound characteristic value; or b) a subset of the respective cardiac pacing sites selected using the heart sound characteristic value, from which subset the preferred pacing site is selected using the Q-LV time interval.

In Example 5, the subject matter of one or any combination of Examples 1-4 optionally includes a signal processing circuit configured to detect a first cardiac signal fiducial indicative of a right ventricular (RV) depolarization and a second cardiac signal fiducial indicative of left ventricular (LV) depolarization and determine a RV-LV time interval between the first cardiac signal fiducial and the second cardiac signal fiducial, and optionally includes a pacing site locating circuit configured to generate an indication of a preferred pacing site as one of: a) a subset of the respective cardiac pacing sites selected using the RV-LV time interval, from which subset the preferred pacing site is selected using the heart sound characteristic value; or b) a subset of the respective cardiac pacing sites selected using the heart sound characteristic value, from which subset the preferred pacing site is selected using the RV-LV time interval.

In Example 6, the subject matter of one or any combination of Examples 1-6 optionally includes a signal processing circuit configured to detect a first cardiac signal fiducial indicative of atrial depolarization and a second cardiac signal fiducial indicative of left ventricular depolarization and determine an A-V delay between the first cardiac signal fiducial and the second cardiac signal fiducial, and optionally includes a pacing site locating circuit configured to generate an indication of a preferred pacing site as one of: a) a subset of the respective cardiac pacing sites selected using the A-V delay, from which subset the preferred pacing site is selected using the heart sound characteristic value; or b) a subset of the respective cardiac pacing sites selected using the heart sound characteristic value, from which subset the preferred pacing site is selected using the A-V delay.

In Example 7, the subject matter of one or any combination of Examples 1-6 optionally includes a cardiac signal sensing circuit, a stimulus circuit and a control circuit included in an implantable medical device connectable to a plurality of electrodes, and combinations of the plurality of electrodes correspond to the plurality of pacing sites.

In Example 8, the subject matter of one or any combination of Examples 1-6 optionally includes a cardiac signal sensing circuit, a stimulus circuit and a control circuit included in a pacing system analyzer, and the pacing system analyzer is connectable to one or more leads including at least one electrode configured for positioning at the pacing sites.

In Example 9, the subject matter of one or any combination of Examples 1-6 optionally includes a cardiac signal sensing circuit and a stimulus circuit included in an implantable medical device that is connectable to a plurality of electrodes, and combinations of the plurality of electrodes correspond to the plurality of pacing sites. The subject matter also optionally includes the control circuit and a pacing site locating circuit included in an external device used to program the implantable medical device.

In Example 10, the subject matter of one or any combination of Examples 1-9 optionally includes a control circuit configured to recurrently change delivery of electrical pacing stimulus therapy to a determined preferred pacing site according to a specified schedule.

Example 11 can include subject matter (such as a method, a means for performing acts, or a machine-readable medium including instructions that, when performed by the machine, cause the machine to perform acts), or can optionally be combined with the subject matter of one or any combination of Examples 1-10 to include such subject matter, comprising sensing a plurality of cardiac signals, from respective cardiac pacing sites, wherein a cardiac signal is representative of electrical cardiac activity, determining intrinsic ventricular activation time interval values for the sensed cardiac signals, sensing, at the respective cardiac pacing sites, a plurality of paced heart sound signals representative of mechanical cardiac activity resulting from an electrical stimulus delivered at the corresponding cardiac pacing site, determining values of a heart sound characteristic for the sensed heart sound signals, and generating an indication of a preferred pacing site, selected from the respective cardiac pacing sites, as at least one of: a) a subset of the respective cardiac pacing sites selected using the intrinsic ventricular activation time interval value, from which subset the preferred pacing site is selected using the heart sound characteristic value; or b) a subset of the respective cardiac pacing sites selected using the heart sound characteristic value, from which subset the preferred pacing site is selected using the ventricular activation time interval value.

In Example 12, the subject matter of Example 11 can optionally include determining values of S1 heart sound amplitude resulting from the pacing stimulus, and generating an indication of a preferred pacing site as at least one of: a) a subset of the respective cardiac pacing sites selected using the intrinsic ventricular activation time interval value, from which subset the preferred pacing site is selected using a value of S1 heart sound amplitude; or b) a subset of the respective cardiac pacing sites selected using a value of S1 heart sound amplitude, from which subset the preferred pacing site is selected using the ventricular activation time interval value.

In Example 13, the subject matter of one or any combination of Examples 11 and 12 can optionally include the values of S1 heart sound amplitude that are values of a difference in amplitude between an intrinsic S1 heart sound and a paced S1 heart sound.

In Example 14, the subject matter of one or any combination of Examples 11-13 optionally includes the ventricular activation time interval as a time interval between a first signal fiducial indicative of a Q-wave and a second signal fiducial indicative of left ventricular depolarization (Q-LV time interval), and the method includes generating an indication of a preferred pacing site as at least one of: a) a subset of the respective cardiac pacing sites selected using the intrinsic Q-LV time interval, from which subset the preferred pacing site is selected using the heart sound characteristic value; or b) a subset of the respective cardiac pacing sites selected using the heart sound characteristic value, from which subset the preferred pacing site is selected using the intrinsic Q-LV time interval.

In Example 15, the subject matter of one or any combination of Examples 11-14 optionally includes the ventricular activation time interval as a time interval between a first signal fiducial indicative of right ventricular depolarization and a second signal fiducial indicative of left ventricular depolarization (RV-LV time interval), and the method includes generating an indication of a preferred pacing site as at least one of: a) a subset of the respective cardiac pacing sites selected using the intrinsic RV-LV time interval, from which subset the preferred pacing site is selected using the heart sound characteristic value; or b) a subset of the respective cardiac pacing sites selected using the heart sound characteristic value, from which subset the preferred pacing site is selected using the intrinsic RV-LV time interval.

In Example 16, the subject matter of one or any combination of Examples 11-15 optionally includes the ventricular activation time interval as a time interval between a first signal fiducial indicative of atrial depolarization and a second cardiac signal fiducial indicative of left ventricular depolarization (A-V delay interval), and the method includes generating an indication of a preferred pacing site as at least one of: a) a subset of the respective cardiac pacing sites selected using the intrinsic A-V delay interval, from which subset the preferred pacing site is selected using the heart sound characteristic value; or b) a subset of the respective cardiac pacing sites selected using the heart sound characteristic value, from which subset the preferred pacing site is selected using the intrinsic A-V delay interval.

Example 17 includes subject matter (such as an apparatus) or can optionally be combined with the subject matter of one or any combination of Examples 1-16 to include such subject matter, comprising a cardiac signal sensing circuit configured to sense a plurality of cardiac signals, from respective cardiac pacing sites, wherein a cardiac signal is representative of electrical cardiac activity; a stimulus circuit configured to provide an electrical cardiac pacing stimulus to the plurality of pacing sites; and a control circuit electrically coupled to the cardiac signal sensing circuit and the stimulus circuit. The control circuit optionally includes a capture detection circuit configured to detect cardiac capture, a signal processing circuit configured to determine intrinsic ventricular activation time interval values for the sensed cardiac signals, and a pacing site locating circuit configured to generate an indication of a preferred pacing site as one of: a) a subset of the respective cardiac pacing sites selected using the intrinsic ventricular activation time interval value, from which subset the preferred pacing site is selected according to whether delivery of the pacing stimulus at a pacing site causes cardiac capture; or b) a subset of the respective cardiac pacing sites selected according to whether delivery of the pacing stimulus at a pacing site causes cardiac capture, from which subset the preferred pacing site is selected using the ventricular activation time interval value.

In Example 18 the subject matter of Example 17 can optionally include a signal processing circuit configured to detect a first cardiac signal fiducial indicative of a Q-wave, a second cardiac signal fiducial indicative of left ventricular (LV) depolarization and determine a Q-LV time interval between the first cardiac signal fiducial and the second cardiac signal fiducial, and can include a pacing site locating circuit optionally configured to generate an indication of a preferred pacing site as one of: a) a subset of the respective cardiac pacing sites selected using the Q-LV time interval, from which subset the preferred pacing site is selected according to whether delivery of the pacing stimulus at a pacing site causes cardiac capture; or b) a subset of the respective cardiac pacing sites selected according to whether delivery of the pacing stimulus at a pacing site causes cardiac capture, from which subset the preferred pacing site is selected using the Q-LV time interval.

In Example 19, the subject matter of one or any combination of Examples 17 and 18 optionally includes a signal processing circuit configured to detect a first cardiac signal fiducial indicative of a right ventricular (RV) depolarization and a second cardiac signal fiducial indicative of left ventricular (LV) depolarization and determine a RV-LV time interval between the first cardiac signal fiducial and the second cardiac signal fiducial, and can optionally include a pacing site locating circuit configured to generate an indication of a preferred pacing site as one of: a) a subset of the respective cardiac pacing sites selected using the RV-LV time interval, from which subset the preferred pacing site is selected according to whether delivery of the pacing stimulus at a pacing site causes cardiac capture; or b) a subset of the respective cardiac pacing sites selected according to whether delivery of the pacing stimulus at a pacing site causes cardiac capture from which subset the preferred pacing site is selected using the RV-LV time interval.

In Example 20, the subject matter of one or any combination of Examples 17-19 optionally includes a signal processing circuit configured to detect a first cardiac signal fiducial indicative of atrial depolarization and a second cardiac signal fiducial indicative of left ventricular depolarization and determine an A-V delay between the first cardiac signal fiducial and the second cardiac signal fiducial, and a pacing site locating circuit optionally configured to generate an indication of a preferred pacing site as one of: a) a subset of the respective cardiac pacing sites selected using the A-V delay, from which subset the preferred pacing site is selected according to whether delivery of the pacing stimulus at a pacing site causes cardiac capture; or b) a subset of the respective cardiac pacing sites selected according to whether delivery of the pacing stimulus at a pacing site causes cardiac capture, from which subset the preferred pacing site is selected using the A-V delay.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
a control circuit configured to:
receive S1 heart sound information of a parameter of an S1 heart sound for each of a plurality of different cardiac pacing site configurations;
determine candidate pacing sites using the received S1 heart sound information;
receive information of electrical depolarization for the candidate pacing sites;
generate pacing site configuration information using the S1 heart sound information and the electrical depolarization information;
present the pacing site configuration information to a user; and
receive a selection of a pacing site configuration in response to presenting the pacing configuration information.

2. The apparatus of claim 1, including a stimulus circuit configured to provide an electrical pacing stimulus to a plurality of cardiac pacing sites when electrically coupled to a plurality of electrodes for arrangement at the cardiac pacing sites; and
a heart sound sensing circuit configured to produce a sensed heart sound signal representative of mechanical cardiac activity.

3. The apparatus of claim 1, wherein the S1 heart sound parameter includes an amplitude of a paced S1 heart sound.

4. The apparatus of claim 1, wherein the S1 heart sound parameter includes an amplitude of an intrinsic S1 heart sound.

5. The apparatus of claim 1, wherein the S1 heart sound parameter includes a difference between an amplitude of a paced S1 heart sound and an amplitude of a sensed S1 heart sound.

6. The apparatus of claim 1, including:
a cardiac signal sensing circuit configured to generate a sensed cardiac signal at a plurality of pacing sites when electrically coupled to a plurality of electrodes for arrangement at the cardiac pacing sites;
wherein the control circuit is configured to:
initiate a measurement of a time interval between intrinsic right ventricular (RV) depolarization and intrinsic left ventricular (LV) depolarization using the sensed cardiac signal as the information of electrical depolarization; and generate an indication of selection of the pacing site configuration based on the measured time interval and the S1 heart sound information.

7. The apparatus of claim 1, including:

a cardiac signal sensing circuit configured to generate a sensed cardiac signal at a plurality of cardiac pacing sites when electrically coupled to a plurality of electrodes for arrangement at the cardiac pacing sites;

wherein the control circuit is configured to:

initiate a measurement of a time interval between a Q-wave and left ventricular activation using the sensed cardiac signal as the information of electrical depolarization; and generate an indication of identification of the pacing site configuration based on the measured time interval and the S1 heart sound information.

8. The apparatus of claim 1, including:

a cardiac signal sensing circuit configured to generate a sensed cardiac signal at a plurality of cardiac pacing sites when electrically coupled to a plurality of electrodes for arrangement at the cardiac pacing sites;

wherein the control circuit is configured to:

initiate a measurement of a time interval between an R-wave detected using the sensed cardiac signal and an intrinsic S1 heart sound detected using the heart sound signal as the information of electrical depolarization; and generate an indication of identification of the pacing site configuration based on the measured time interval and the S1 heart sound information.

9. The apparatus of claim 1, including:

a cardiac signal sensing circuit configured to generate a sensed cardiac signal at a plurality of cardiac pacing sites when electrically coupled to a plurality of electrodes for arrangement at the cardiac pacing sites;

wherein the control circuit is configured to:

measure a capture threshold of one or more of the plurality of pacing sites using the sensed cardiac signal as the information of electrical depolarization; and generate an indication of identification of the pacing site configuration based on the measured capture threshold and the S1 heart sound information.

10. The apparatus of claim 1, including:

a stimulus circuit configured to provide an electrical pacing stimulus to the plurality of pacing sites; and a heart sound sensing circuit configured to produce a sensed heart sound signal representative of mechanical cardiac activity;

wherein the stimulus circuit and the heart sound sensing circuit are included in a medical device, the control circuit is included in a medical device programmer, and the control circuit is configured to initiate programming of the medical device with the received pacing site configuration.

11. A method of controlling operation of a medical device system, the method comprising:

receiving S1 heart sound information of a parameter of an S1 heart sound for each of a plurality of different cardiac pacing site configurations;

determining candidate pacing sites using the received S1 heart sound information;

receiving information of electrical depolarization for the candidate pacing sites;

generating pacing site configuration information using the S1 heart sound information and the electrical depolarization information;

presenting the pacing site configuration information to a user; and receiving a selection of a pacing site configuration in response to presenting the pacing configuration information.

12. The method of claim 11, including:

providing an electrical pacing stimulus to the plurality of cardiac pacing sites; and wherein receiving the S1 heart sound information includes producing a sensed heart sound signal.

13. The method of claim 11, wherein the S1 heart sound parameter includes an amplitude of a paced S1 heart sound.

14. The method of claim 11, wherein the S1 heart sound parameter includes an amplitude of an intrinsic S1 heart sound.

15. The method of claim 11, wherein the S1 heart sound parameter includes a difference between an amplitude of a paced S1 heart sound and an amplitude of a sensed intrinsic S1 heart sound.

16. The method of claim 11, including:

generating a sensed cardiac signal for each of a plurality of candidate pacing sites using the medical device system;

measuring a time interval between intrinsic right ventricular (RV) depolarization and intrinsic left ventricular (LV) depolarization using the sensed cardiac signal as the information of electrical depolarization; and generating an indication of selection of the pacing site configuration based on the measured time interval and the S1 heart sound information.

17. The method of claim 11, including:

generating a sensed cardiac signal for each of a plurality of candidate pacing sites using the medical device system;

measuring a time interval between a Q-wave and left ventricular activation using the sensed cardiac signal as the information of electrical depolarization; and generating an indication of identification of the pacing site based on the measured time interval and the S1 heart sound information.

18. The method of claim 11, including:

generating a sensed cardiac signal for each of a plurality of pacing sites using the medical device system;

measuring a time interval between an R-wave detected using the sensed cardiac signal and an intrinsic S1 heart sound detected using the heart sound signal as the information of electrical depolarization; and generating an indication of identification of the pacing site based on the measured time interval and the S1 heart sound information.

19. The method of claim 11, including:

generating a sensed cardiac signal for each of a plurality of pacing sites using the medical device system;

measuring a capture threshold of the pacing sites using the sensed cardiac signal as the information of electrical depolarization; and generating an indication of identification of the pacing site based on the measured capture threshold and the S1 heart sound information.

20. The method of claim 11, including:

providing an electrical pacing stimulus to the plurality of cardiac pacing sites using a medical device of the medical device system;

producing a sensed heart sound signal representative of mechanical cardiac activity; and programming, using a medical device programmer of the medical device system, the medical device with the received pacing site configuration.

* * * * *